United States Patent [19]

Nakatsugawa et al.

[11] Patent Number: 5,350,684
[45] Date of Patent: Sep. 27, 1994

[54] EXTREMELY HALOPHILIC METHANOGENIC ARCHAEBACTERIA

[75] Inventors: Naoki Nakatsugawa, Wako; Koki Horikoshi, Tokyo, both of Japan

[73] Assignees: Research Development Corporation of Japan; Mitsubishi Electric Corporation, both of Tokyo; Rikagaku Kenkysuho, Wako, all of Japan; a part interest

[21] Appl. No.: 668,157

[22] Filed: Mar. 12, 1991

Related U.S. Application Data

[62] Division of Ser. No. 255,015, Oct. 7, 1988, Pat. No. 5,055,406.

[30] Foreign Application Priority Data

Oct. 9, 1987 [JP] Japan .................. 62-255995

[51] Int. Cl.⁵ .................. C12N 1/20; C12N 5/02; C12P 5/02
[52] U.S. Cl. .................. 435/167; 435/252.1; 435/822
[58] Field of Search .................. 435/252.1, 822, 167

[56] References Cited

FOREIGN PATENT DOCUMENTS 0332134  9/1989  European Pat. Off. .......... 435/167
1175000  8/1986  Japan .......................... 435/167

OTHER PUBLICATIONS

Chem Abs vol 108, 71972c (1988).
Chem Abs vol 106, 172626g (1987).
Chem Abs vol 105, 57603q (1986).
Dokl. Akad. Nauk. USSR vol 293 pp. 464–468 (1987).
Int. J. of Systematic Bact. vol. 38, pp. 122–123 (1988).
Int. J. of Symstematic Bact vol. 38 pp. 139–142 (1988).
Stronach et al, *Anaerobic Digestion Processes in Industrial Wastewater Treatment,* Springer-Verlag, N.Y., pp. 59–63 (1986).

*Primary Examiner*—Herbert J. Lilling
*Attorney, Agent, or Firm*—Oblon, Spivak, McClelland, Maier & Neustadt

[57] ABSTRACT

Methanohalococcus alcaliphilum having an optimum growth sodium chloride concentration ranging from about 2.5 to about 3 mole are herein disclosed. The bacteria are halophilic or halophilic and alkalophilic and can be used as the microorganisms which play a central role in the methods of methane fermentation to enhance the efficiency of such a method since the use of the microorganism makes it possible to carry out the method at an alkaline pH, in the presence of salts in a high concentration and at a low temperature.

3 Claims, 8 Drawing Sheets

EXTREMELY HALOPHILIC METHANOGENIC ARCHAEBACTERIA

This is a division, of application Ser. No. 07/255,015, filed on Oct. 7, 1988 now U.S. Pat. No. 5,055,406.

BACKGROUND OF THE INVENTION

1. Field of the Invention

The present invention relates to extremely halophilic methanogenic bacteria and more particularly a new genes and new species, Methanohalococcus alcaliphilum having an optimum growth in concentrations of sodium chloride ranging from about 2.5M to 3.0M.

2. Description of the Prior Art

Examples of the halophilic methanogenic bacteria conventionally known include those having an optimum growth at a sodium chloride concentration which ranges from 1 to 2M (Applied and Environmental Microbiology, 1985, Vol. 50, No. 4, pp. 877–881); those having an optimum growth sodium chloride concentration which ranges from 1.2 to 1.5M (Microbiology (U.S.S.R.), 1983, Vol. 52, pp. 290–297); and those having an optimum sodium chloride concentration of 2.1M (Applied and Environmental Microbiology, 1985, Vol. 50, No. 1, pp. 140–143). Although all of these bacteria are halophilic, the sodium chloride concentration among the optimum growth conditions thereof is not more than 2.1M and thus they are moderately-halophilic methanogenic bacteria.

SUMMARY OF THE INVENTION

Accordingly, it is an object of the present invention to provide methane orgenic bacteria having an optimum growth in sodium chloride concentrations higher than that of the aforementioned known methane orgenic bacteria. More specifically, the principal object of the present invention is to provide a alcaliphilum having optimum growth new genus and new species Methanohalococcus at high sodium chloride concentrations.

Another object of the present invention is to eliminate disadvantages encountered in carrying out methods of methane gas production (methane fermentation) in order to improve the efficiency thereof.

Consequently, the present invention relates to Halomethanococcus alcaliphilum having an optimum growth at sodium chloride concentrations ranging from about 2.5M to 3.0M.

BRIEF DESCRIPTION OF THE ACCOMPANYING DRAWINGS

The microorganisms of the present invention will hereunder be explained in more detail with reference to the accompanying drawings, wherein.

DETAILED DESCRIPTION OF THE PREFERRED EMBODIMENTS

Methanahalococcus alcaliphilum of the present invention can be classified into two groups: one of which is NY-218 (FERM BP-2079) whose optimum growth pH ranges from about 8.0 to about 8.5 and the other of which is NY-844 (FERM BP-2080) whose optimum growth pH ranges from about 7.5 to about 8.0.

The means for obtaining Methanohalococcus alcaliphilum of the present invention (the screening method or the like) will now be explained in more detail below.

(1) Screening Method

In the present invention, the screening of methanogenic bacteria was carried out in accordance with the methods for separating anaerobic bacteria disclosed in Japanese Patent Application (hereunder referred to as "J.P.A.") Serial No. 61-191541 and Japanese Utility Model Application (hereunder referred to as "J.U.M.A.") Serial No. 61-125086. More specifically, the screening method employed herein comprises the steps of first exploring soil in extreme environments such as soil under a strong alkali condition or a high salt concentration to collect bacteria under the desired special environment; then immediately establishing conditions suitable for the collected bacteria such as anaerobic conditions and low redox potential conditions utilizing a diluent for pretreatment which is prepared on the basis of the solution disclosed in J.P.A. No. 61-191541; preparing a solution for dilution while taking into consideration the characteristics of the soil, from which the bacteria have been collected, such as pH and salt concentration thereof; and finally immediately suspending the soil into the solution for dilution. The suspension thus obtained should be stored in a container as disclosed in J.U.M.A. No. 61-125086 so that the methanogenic bacteria, i.e., strictly anaerobic bacteria do not die out and simultaneously it should be transported while maintaining it so that the objective methane producing bacteria in a special environment do not die out. The transported sample is used as the sample for isolation culture.

With regard to the soil as a source for screening, soil in special environments is widely explored in Japan and abroad.

(2) Isolation Culture

As the medium for isolation culture, an isolation medium which was originally developed by the inventors of the present invention is employed. The composition of the isolation medium used is summarized in Table I given below. In this connection, the composition of the solution of trace elements or that of the solution of vitamins included in Table I are listed in Table II or III respectively. Regarding the trace element solution shown in Table II, the requirement of the bacteria for trace elements has not yet been clearly determined and, therefore, a trace element solution is used having an original composition in which the kinds of trace elements used and the amount thereof are increased.

As the substrates to be added to the culture medium, there can be used, as shown in Table I, such substances as sodium formate, sodium acetate, methanol and methylamines (e.g., trimethylamine) and the amount thereof is independently adjusted to 0.5 to 1.0%. Sodium bicarbonate is used to control the pH value of the culture medium when culturing is commenced.

In addition, methanogenic bacteria are archaebacteria and they do not contain peptidoglycan in their cell wall. Therefore, they exhibit no sensitivity to a peptidoglycan synthesis inhibitor. Moreover, they do not have sensitivity to protein synthesis inhibitors effective on bacteria which have a procaryotic cell type 70S ribosome system, though their ribosomes are of the 70S type. Thus, effective isolation of the desired methanogenic bacteria was carried out by adding, to the culture medium, an antibiotic which could suppress the growth of only non-methane producing bacteria during isolation culture. More specifically, vancomycin which is an inhibitor for peptidoglycan synthesis in the cell wall and kanamycin which is a protein synthesis inhibitor effective on bacteria having a procaryotic cell type 70S ribosome system were employed as shown in Table I.

As the gas phase during culture, there were used three kinds of gases, i.e., $H_2/CO_2$ mixed gas (80/20); $N_2/CO_2$ mixed gas (80/20) and $N_2$ gas which were deoxygenated prior to use. Such a gas was charged into a container for culture so that the pressure therein was equal to positive 2 atms. during culture irrespective of the kinds of the culture medium which may be either liquid medium or agar medium, whereby the cultivation is carried out under pressure. Moreover, the culture was principally carried out by stationary culture or culture in the dark.

As described above, the methanogenic bacteria growing under special conditions have widely been searched for. Conditions other than those disclosed above during the isolation culture were as follows: pH=6.5 to 9.0; temperature=10° to 60° C.; and the sodium chloride concentration=1 to 4M. When the isolation culture is conducted at a sodium chloride concentration ranging from 1 to 4M as a condition for isolation culture, the isolation medium is prepared by changing the concentration of magnesium chloride or potassium chloride within the range shown in Table I since the requirements of the bacteria concerned for substances such as magnesium and potassium is unclear.

(3) Identification of the Objective Bacteria

The identification of the objective methanogenic bacteria growing under the extreme environments was effected as follows. The culture is effected according to the aforementioned isolation culture technique at a desired cultivation temperature utilizing a culture medium in which conditions such as pH, the concentration of sodium chloride and kinds of substrates used and to which there are added the aforesaid inhibitor for peptidoglycan synthesis in the cell wall and an antibiotic as a protein synthesis inhibitor effective to bacteria having procaryotic cell type 70S ribosome system in order to isolate only the methane producing bacteria belonging to archaebacteria. The bacteria which would grow during such isolation culture are considered to be one of the following bacteria, so far as can be judged from the composition of the culture medium and the like:

(a) objective methanogenic bacteria;
(b) strictly anaerobic bacteria, which are antibiotic resistant, other than methane producing bacteria; or
(c) archaebateria other than methanogenic bacteira, which are strictly anaerobic or resistant to anaerobic conditions.

The following two methods are adopted to identify only the objective methane producing bacteria from a product of the isolation culture: one of which comprises analyzing gases present in the head space of the container for culture by a means such as gas chromatography to confirm the production of methane gas; and the other of which comprises observing the grown bacteria by a fluorescence microscope to examine the product.

The methanogenic bacteria have a factor $F_{420}$ inherent thereto and emit fluorescent rays of bluish green originated from the factor when they are irradiated with ultraviolet rays of long wave length. Therefore, it can be confirmed whether the grown bacteria are methane producing ones or non-methanogenic ones on the basis of the presence or absence of the emission of fluorescent rays upon irradiating them with ultraviolet rays and examining them by a fluorescence microscope. In this regard, some of the non-methanogenic bacteria emit fluorescent rays, but the fluorescence rays emitted by them are not bluish green but yellowish white or bluish white. Thus, in such cases, the methanogenic bacteria may certainly be distinguished from the non-methanogenic ones.

The objective methanogenic bacteria can be isolated in the pure condition by identifying them according to the foregoing methods and repeating procedures such as dilution and agar plating methods to purify the same.

TABLE I

Composition of the Culture Medium

| Component | Amount (g/l) |
|---|---|
| Dipotassium hydrogenphosphate | 0.7 |
| Ammonium chloride | 1.0 |
| Calcium chloride | 0.1 |
| Magnesium sulfate | 0.2 |
| 2-Mercaptoethane sulfonic acid | 1 (mg/l) |
| Yeast extract (available from Difco Co., Ltd.) | 1.0 |
| Triputicase peptone (available from B.B.L. Co., Ltd.) | 1.0 |
| Casamino acid (available from Difco Co., Ltd.) | 0.5 |
| Cacitone (available from Difco Co., Ltd.) | 1.0 |
| Solution of trace element (see Table II) | 10 (ml/l) |
| Solution of vitamin (see Table III) | 10 (ml/l) |
| Resazurin | 1 (mg/l) |
| L-cystein | 0.45 |
| Sodium sulfide | 0.65 |
| Vancomycin | 0.5 |
| Kanamycin | 0.5 |
| Sodium chloride | 58.4–233.6 |
| Magnesium chloride | 10–20 |
| Potassium chloride | 3–5 |
| DL-Methionine | 1 |
| Sodium formate | 5–10 |
| Sodium acetate | 5–10 |
| Methanol | 5–10 |
| Trimethylamine hydrochloride | 5–10 | see the remark *1) for Sodium formate, Sodium acetate, Methanol, Trimethylamine hydrochloride

*1): In each culture medium, only one of these substrates was used.
*2): In each culture medium, the value of pH was adjusted by the addition of sodium bicarbonate.
*3): Each numerical value in Table I denotes the content of each component per liter of culture medium in which the balance was purified water.

TABLE II

Composition of the Solution of trace element

| Component | Amount (g/l) |
|---|---|
| Ferrous sulfate | 0.3 |
| Cobalt chloride | 0.2 |
| Zinc chloride | 0.1 |
| Boric acid | 0.05 |
| Sodium molybdate | 0.2 |

TABLE II-continued

Composition of the Solution of trace element

| Component | Amount (g/l) |
| --- | --- |
| Manganese chloride | 0.1 |
| Copper sulfate | 0.01 |
| Aluminum potassium sulfate | 0.005 |
| Nitrilotriacetic acid | 2.5 |
| Nickel chloride | 0.5 |
| Sodium selenite | 0.1 |
| Sodium tungstate | 0.1 |
| Cadmium chloride | 0.05 |

*): Each numerical value in Table II denotes the content of each component per liter of culture medium in which the balance was purified water.

TABLE III

Composition of the Solution of Vitamin

| Component | Amount (mg/l) |
| --- | --- |
| Biotin | 2 |
| Folic acid | 2 |
| Pyridoxine | 10 |
| Riboflavin | 5 |
| Thiamin | 5 |
| Pantothenic acid | 5 |
| Cyanocobalamin | 0.1 |
| p-Aminobenzoic acid | 5 |
| Alpha-lipoic acid | 5 |

*): Each numerical value in Table III denotes the content of each component per liter of culture medium in which the balance was purified water.

of each component per liter of culture medium in which the balance was purified water.

(4) Collection of the Objective Microorganisms

The inventors of the present invention tried to isolate desired methanogenic bacteria from soil in special environmental conditions widely collected from Japan and abroad in accordance with the aforementioned methodology. As a result, the inventors could isolate a variety of halophilic or halophilic and alkalophilic methanogenic bacteria from the soil of high salt content collected in the West of the United States of America.

These methanogenic bacteria were cultured and examined. As a result, there were isolated two kinds of extremely halophilic methanogenic bacteria having different optimum growth pH ranges. These microorganisms grow at wide sodium chloride concentrations which range at least from about 1 to 4 m, have the optimum growth concentrations ranging from 2.5 to 3 m and have good methane gas production activity. Thus, these bacteria were confirmed to be extremely halophilic.

It was confirmed that the first methanogenic bacteria NY-218 of the present invention are also alkalophilic since they grow at least at a pH ranging from 7.0 to 9.0, have an optimum growth pH ranging from 8.0 to 8.5 and good methane gas production activity. It was likewise confirmed that these bacteria show the methane gas production activity even under the culture condition of 15 to 45° C. Their optimum growth temperature is in the range of 35° to 37° C.

It was confirmed that the bacteria NY-218 are gram-negative and strictly anaerobic bacteria, which are a motile coccus with flagella having a diameter of 0.5 to 1.5 micron and which never sporulate. Unlike the general bacteria, they are archaebacteria exhibiting no sensitivity to antibiotics or the like which inhibit the peptidoglycan synthesis of the cell wall.

The bacteria NY-218 are capable of assimilating methanol and methylamine at least at a cultivation temperature of 37° C., sodium chloride concentration of 2.5 to 3M and pH of 8.0 to 8.5.

The inventors of this invention deposited the bacteria NY-218 with the Fermentation Research Institute (FRI) (mailing address: Fermentation Research Institute, Agency of Industrial Science and Technology, Yatabemachi, Ibaraki, Japan 305) in accordance with the Budapest Treaty under the accession number of FERM BP-2079 on Oct. 7, 1987.

It is confirmed that the second bacteria NY-844 of the present invention grow at least at a pH ranging from 6.5 to 8.5, that they have the optimum growth pH ranging from 7.5 to 8.0 and good methane gas production activity. Moreover, it was likewise confirmed that the bacteria NY-844 show the methane gas production activity even at a cultivation temperature of 15° to 45° C. and that their optimum growth temperature is in the range of 35° to 37° C.

It was confirmed that the bacteria NY-844 are gram-negative and strictly anaerobic bacteria, which are a motile coccus having a diameter of 0.5 to 1.5 micron, and which never sporulate. Unlike the general bacteria, they are archaebacteria exhibiting no sensitivity to antibiotics or the like which inhibit the peptidoglycan synthesis in the cell wall.

The bacteria NY-844 are capable of assimilating methanol and methylamine at least at a cultivation temperature of 37° C., sodium chloride concentration ranging from 2.5 to 3M and pH ranging from 7.5 to 8.0.

The inventors of this invention deposited the bacteria NY-844 with the same Fermentation Research Institute (FRI) mentioned above in accordance with the Budapest Treaty under the accession number of FERM BP-2080 on October 7, Showa 62 (1987).

The present invention will hereunder be explained in more detail with reference to the following non-limiting working Examples.

EXAMPLE 1-1

This Example was carried out to examine the influence of the sodium chloride concentration on the amount of methane gas produced by the bacterium NY-218 of the present invention collected in the manner as discussed above when cultured in a culture medium whose composition was shown in Table I and in which the substrate was 0.8% trimethylamine and the sodium chloride concentration was changed within the range of 1 to 4M. The cultivation was effected at 37° C. for 15 days. The results obtained are plotted in FIG. 1, with the sodium chloride concentration (M) in the culture medium as the abscissa and the amount of methane gas (m mole) generated as the ordinate.

Figure 1:
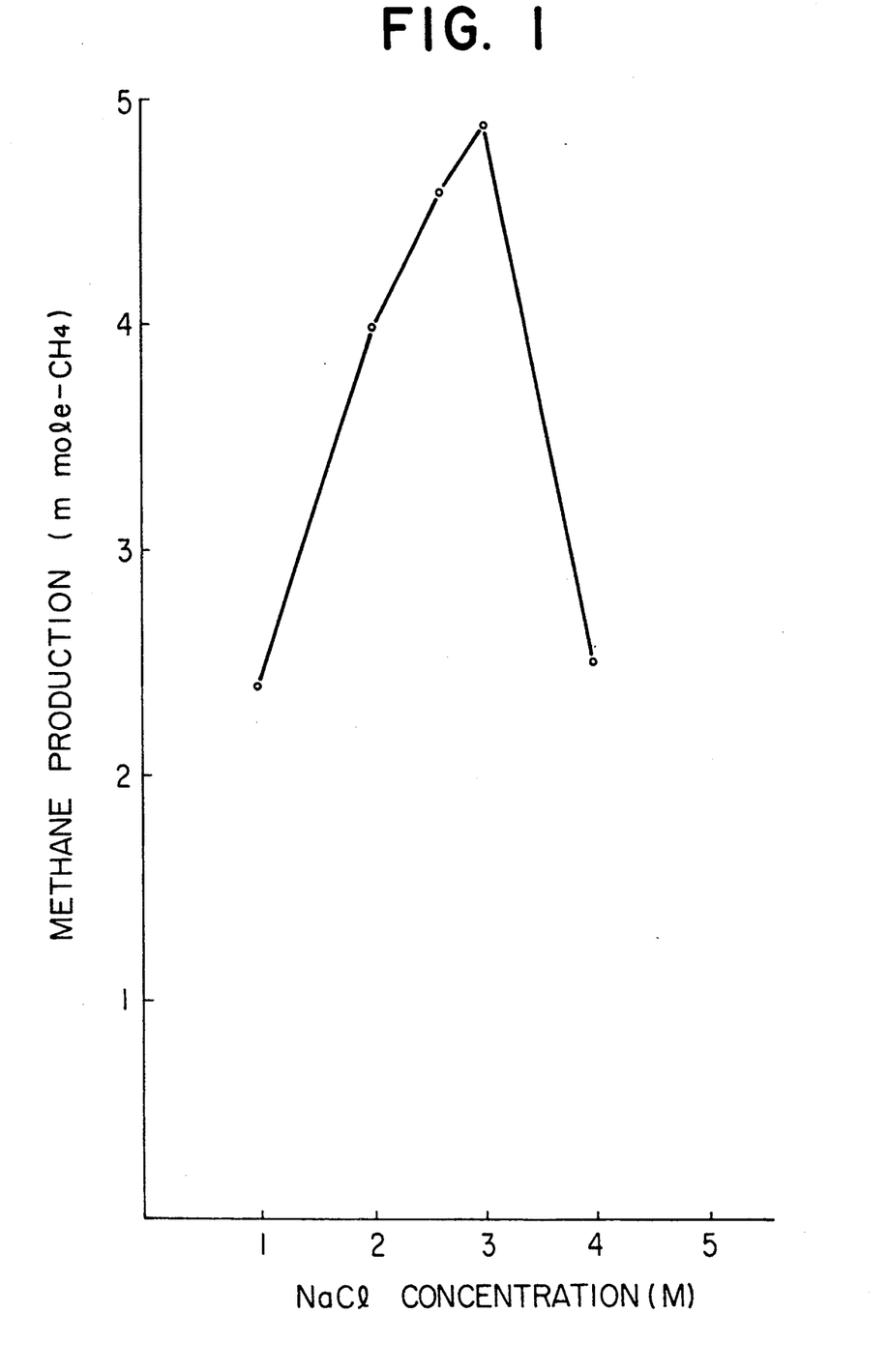
FIGS. 1 to 4 are diagrams in which the amount of methane gas produced by the methane orgenic bacteria NY-218 of the present invention is plotted against NaCl concentration, pH, temperature and cultivation days respectively.

As seen from the results shown in FIG. 1, it is appreciated that the bacteria NY-218 grow at a sodium chloride concentration ranging from 1 to 4M and that their optimum growth concentration of sodium chloride ranges from 2.5 to 3M.

EXAMPLE 1-2

This Example was carried out to examine the influence of pH on the amount of methane gas produced by the bacteria NY-218 of the present invention collected by the manner as discussed above when cultured in a culture medium whose composition was shown in Table I and in which the substrate was 0.8% trimethylamine and the pH value was changed within the range of 6.5 to 9.0. The cultivation was effected at 37° C. for 15 days. The results obtained are plotted in FIG. 2, with the pH value of the culture medium as the abscissa and the amount of methane gas produced (m mole) as the ordinate.

Figure 2:
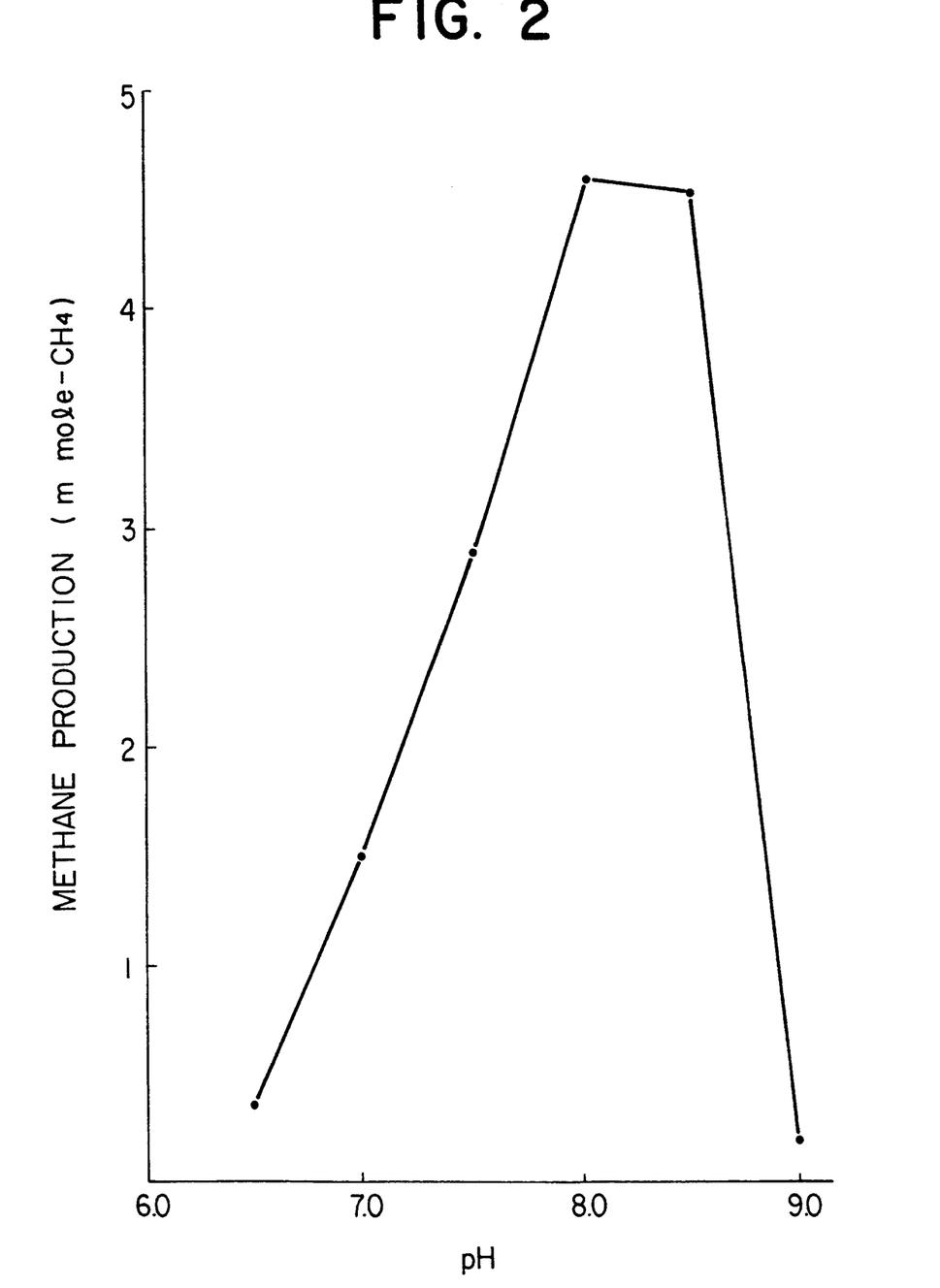

As seen from the results shown in FIG. 2, it is appreciated that the bacteria NY-218 grow at a pH value ranging from 7.0 to 9.0 and that the optimum growth pH condition thereof ranges from 8.0 to 8.5.

EXAMPLE 1-3

This Example was carried out to examine the influence of temperature on the amount of methane gas produced by the bacteria NY-218 of the present invention collected in the manner as discussed above when they were cultured in a culture medium whose composition was shown in Table I, in which the substrate was 0.8% trimethylamine, and whose temperature was changed within the range of 15° to 60° C. The cultivation was continued for 15 days. The results obtained are plotted in FIG. 3, with the temperature of the culture medium as abscissa and the amount of methane gas (m mole) generated as ordinate.

Figure 3:
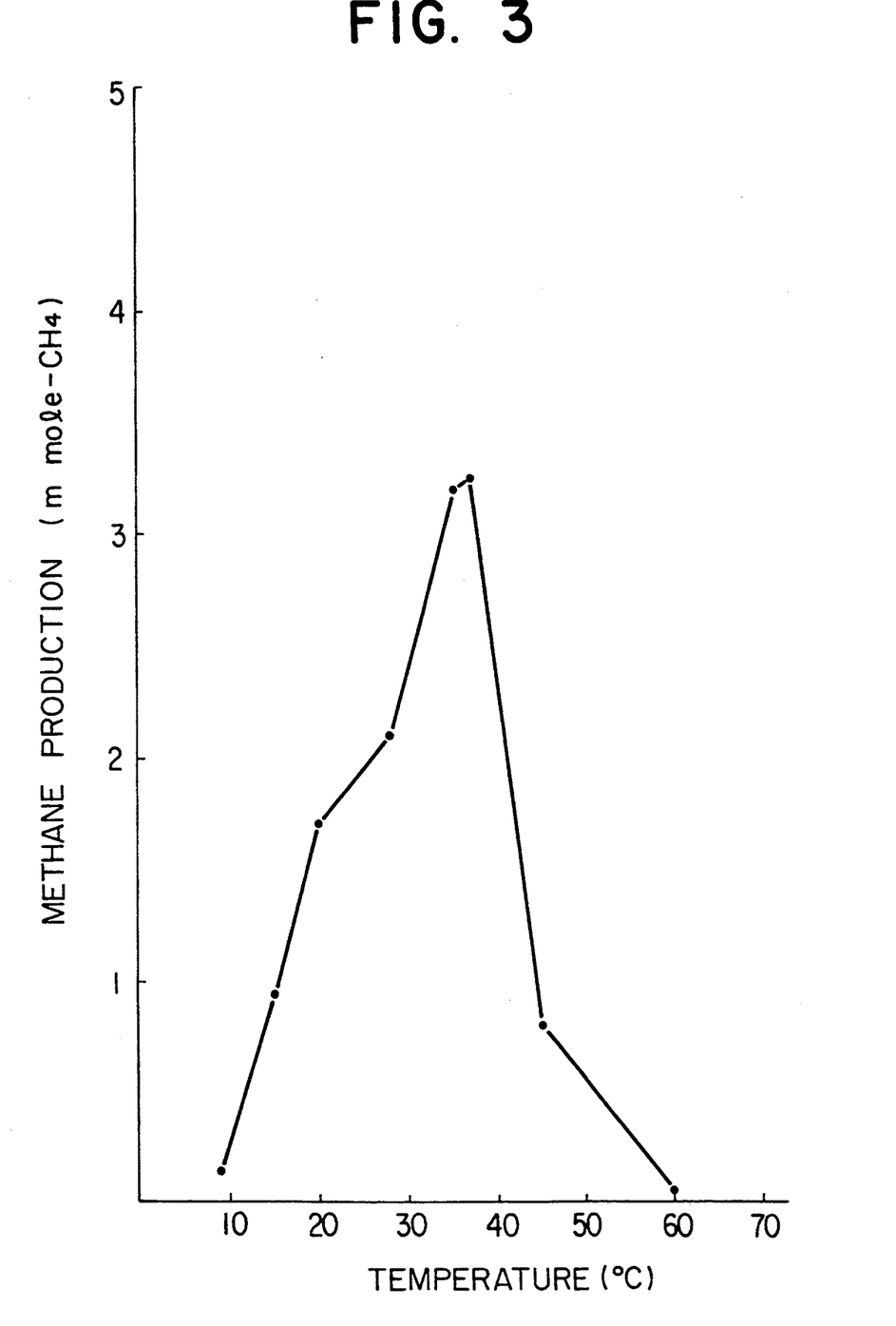

As seen from the results shown in FIG. 3, it is appreciated that the bacteria NY-218 grow at a temperature of the culture medium ranging from 15° to 45° C. and that the optimum growth temperature condition thereof approximately ranges from 35° to 37° C.

EXAMPLE 1-4

Figure 4:
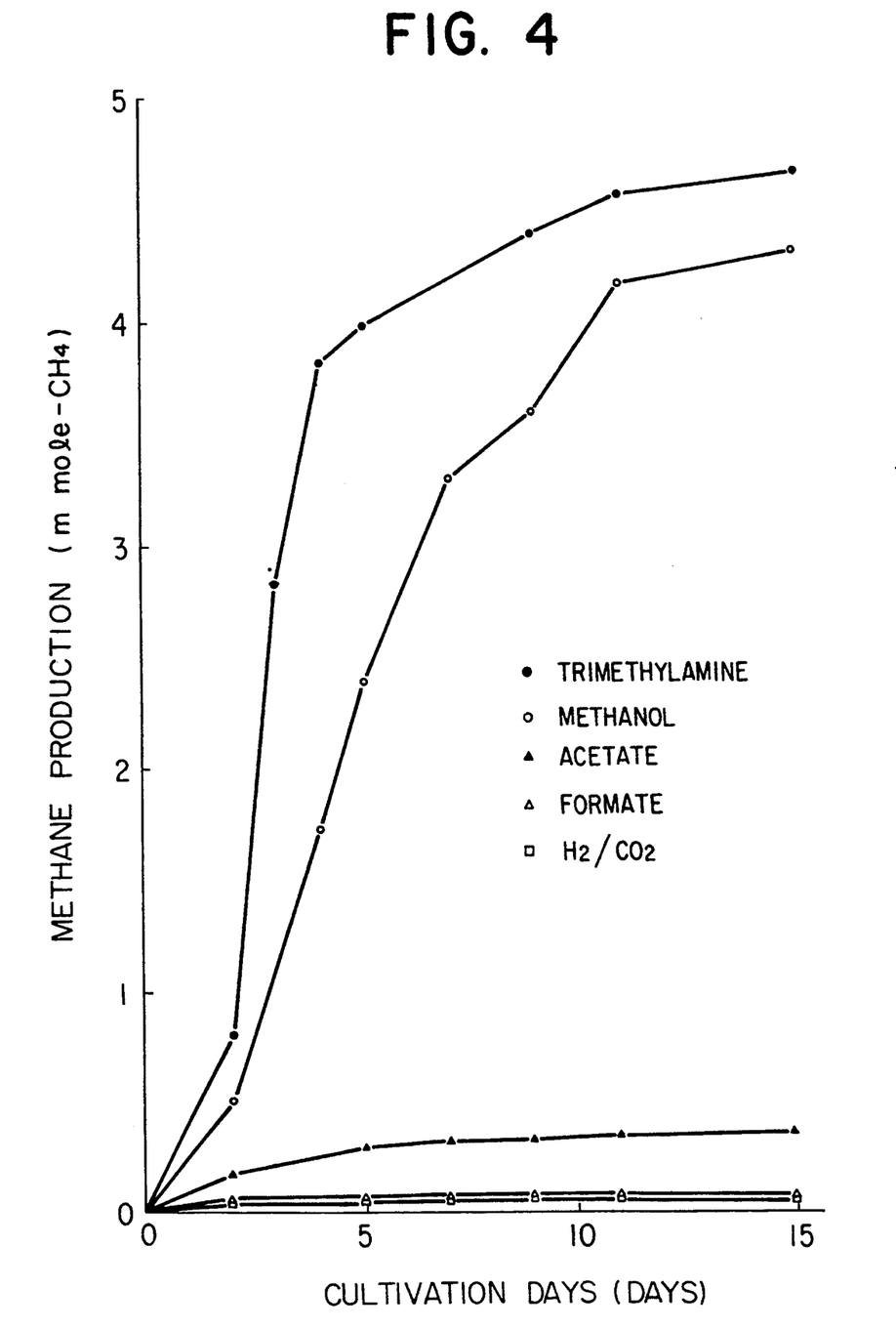

This Example was carried out to examine the influence of the kinds of substrates used on the amount of methane gas generated by the bacteria NY-218 of the present invention collected in the manner as discussed above when they were cultured in a culture medium whose composition was shown in Table I and in which the substrate used was one member selected from the group consisting of sodium formate, sodium acetate, methanol, trimethylamine and $H_2/CO_2$. In these cases, the gas phase used for the culture was $N_2$ (2 atm.; positive) except for the case where $H_2/CO_2$ was used as the substrate. When the substrate was $H_2/CO_2$, it was not added to the culture medium but was used as the gas phase (2 atm.; positive). In this Example, pH was 8.2, the sodium chloride concentration was 3M and the cultivation temperature was 37° C.

The results obtained are plotted in FIG. 4, with the cultivation days as the abscissa and the amount of methane gas (m mole) generated as the ordinate and are also summarized in Table IV given below.

EXAMPLE 1-5

The bacteria NY-218 of the present invention were cultured in a culture medium whose composition was shown in Table I and in which the substrate was 0.8% of trimethylamine. Then, the generation time thereof was estimated from the amount of methane gas generated and it was found to be 5 to 10 hours.

EXAMPLE 2-1

This Example was carried out to examine the influence of the sodium chloride concentration on the amount of methane gas generated by the bacteria NY-844 of the present invention collected in the manner as discussed above when they were cultured in a culture medium whose composition was shown in Table I and in which the substrate was 0.8% trimethylamine and the sodium chloride concentration was changed within the range of 1 to 4M. The cultivation was effected at 37° C. for 15 days. The results obtained are plotted in FIG. 5, with the sodium chloride concentration (M) in the culture medium as abscissa and the amount of methane gas produced (m mole) as ordinate.

Figure 5:
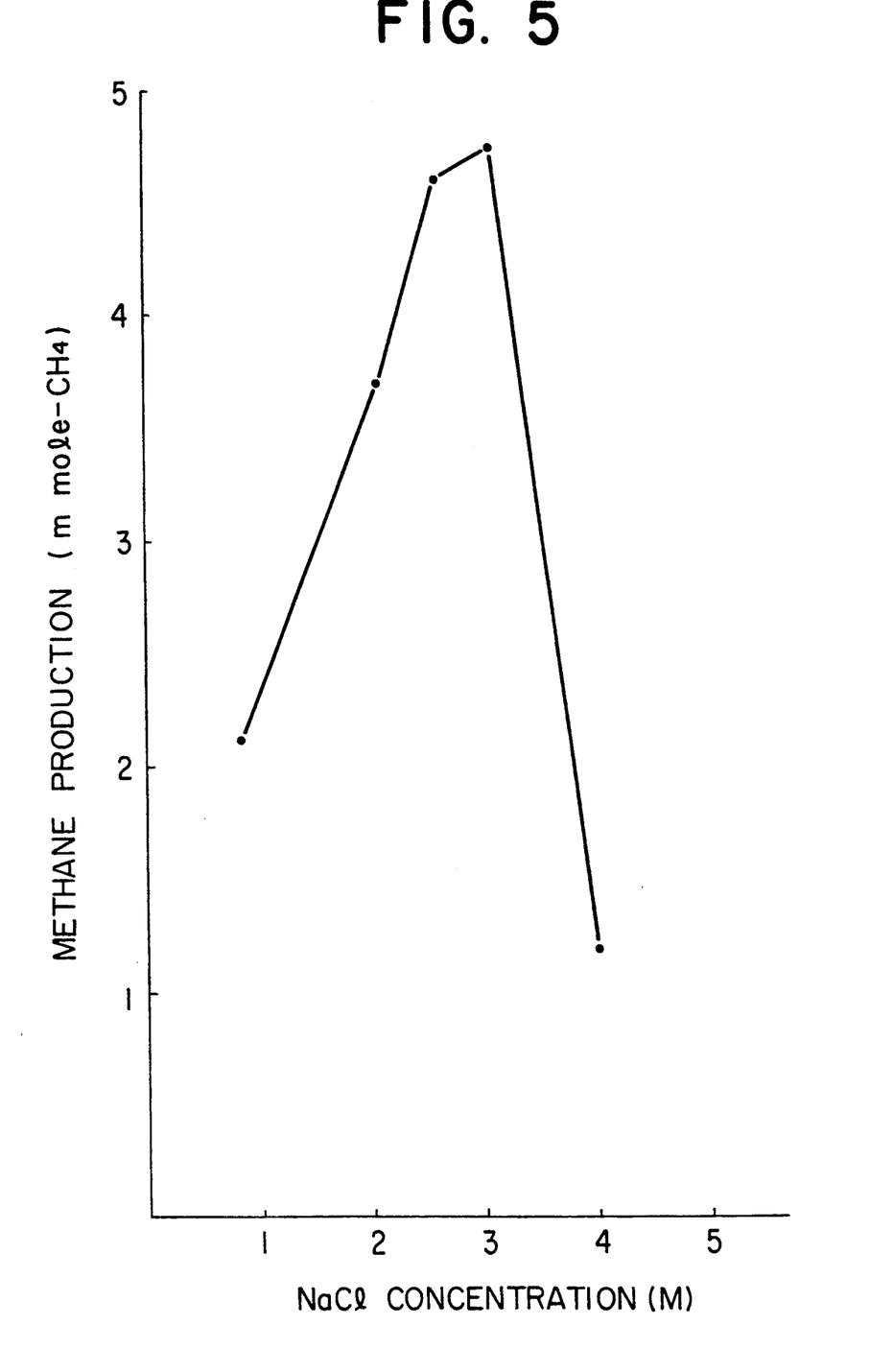
FIGS. 5 to 8 are diagrams similar to FIGS. 1 to 4 except that the methane orgenic bacteria NY-844 of the present invention are used instead of NY-218.

As seen from the results shown in FIG. 5, it is appreciated that the bacteria NY-844 grow at a sodium chloride concentration ranging from 1 to 4M and that their optimum growth concentration of sodium chloride ranges from 2.5 to 3M.

EXAMPLE 2-2

This Example was carried out to examine the influence of pH on the amount of methane gas generated by the bacteria NY-844 of the invention collected in the manner as discussed above when cultured in a culture medium whose composition was as shown in Table I and in which the substrate was 0.8% trimethylamine and the pH value was changed within the range of 6.5 to 8.5. The cultivation was effected at 37° C. for 15 days. The results obtained are plotted in FIG. 6, with the pH value of the culture medium as the abscissa and the amount of methane gas produced (m mole) as the ordinate.

Figure 6:
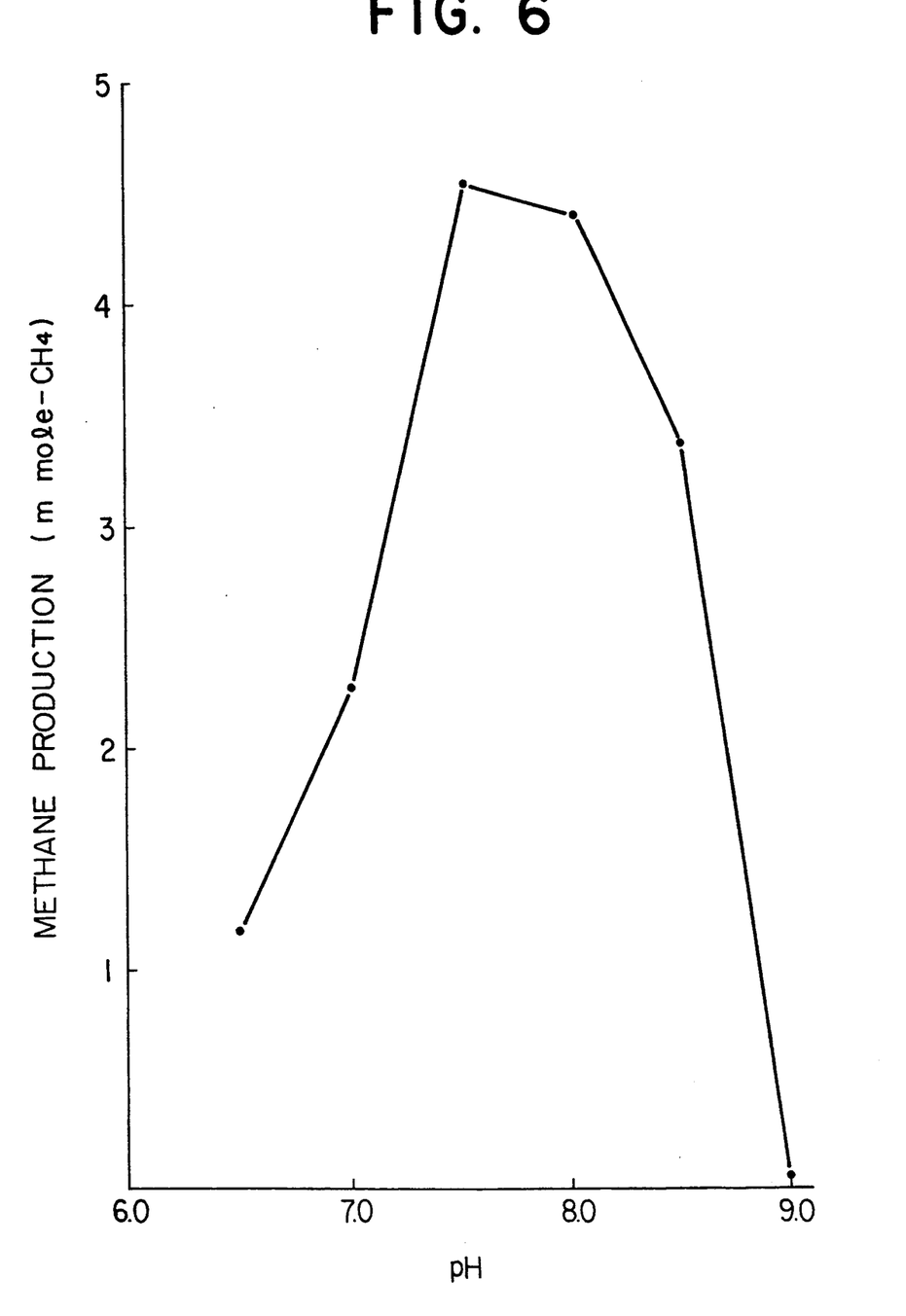

As seen from the results shown in FIG. 6, it is appreciated that the bacteria NY-844 grow at a pH value ranging from 6.5 to 8.5 and that their optimum growth pH condition ranges from 7.5 to 8.0.

EXAMPLE 2-3

This Example was carried out to examine the influence of temperature on the amount of methane gas generated by the bacteria NY-844 of the present invention, collected in the manner as discussed above, when cultured in a culture medium whose composition was as shown in Table I, in which the substrate was 0.8% trimethylamine and whose temperature was changed within the range of 15° to 60° C. The cultivation was continued for 20 days. The results obtained are plotted in FIG. 7, with the temperature of the culture medium as the abscissa and the amount of methane gas (m mole) generated as the ordinate.

Figure 7:
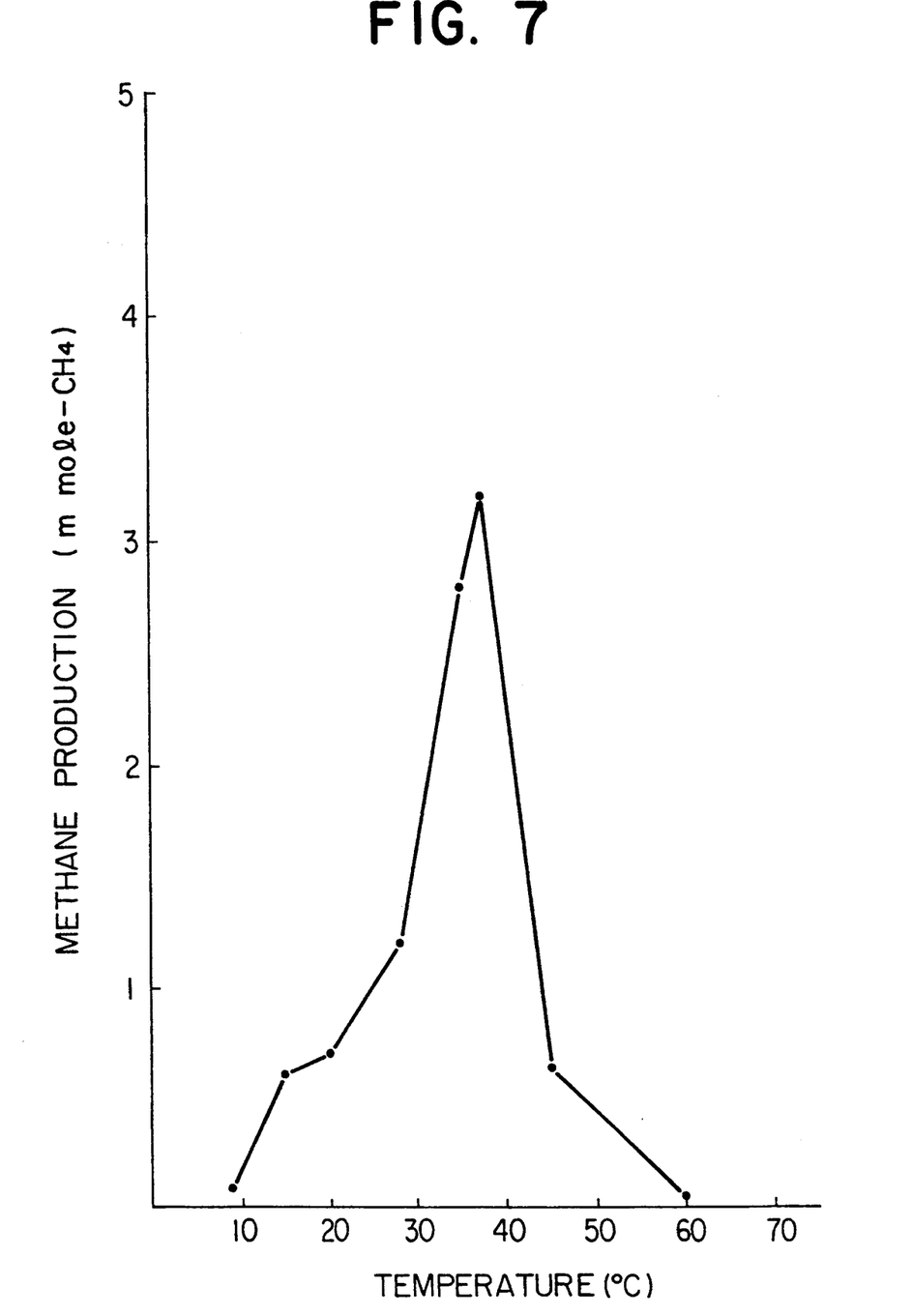

As seen from the results shown in FIG. 7, it is appreciated that the bacteria NY-844 grow at a temperature of the culture medium ranging from 15° to 45° C. and that their optimum growth temperature condition approximately ranges from 35° to 37° C.

EXAMPLE 2-4

Figure 8:
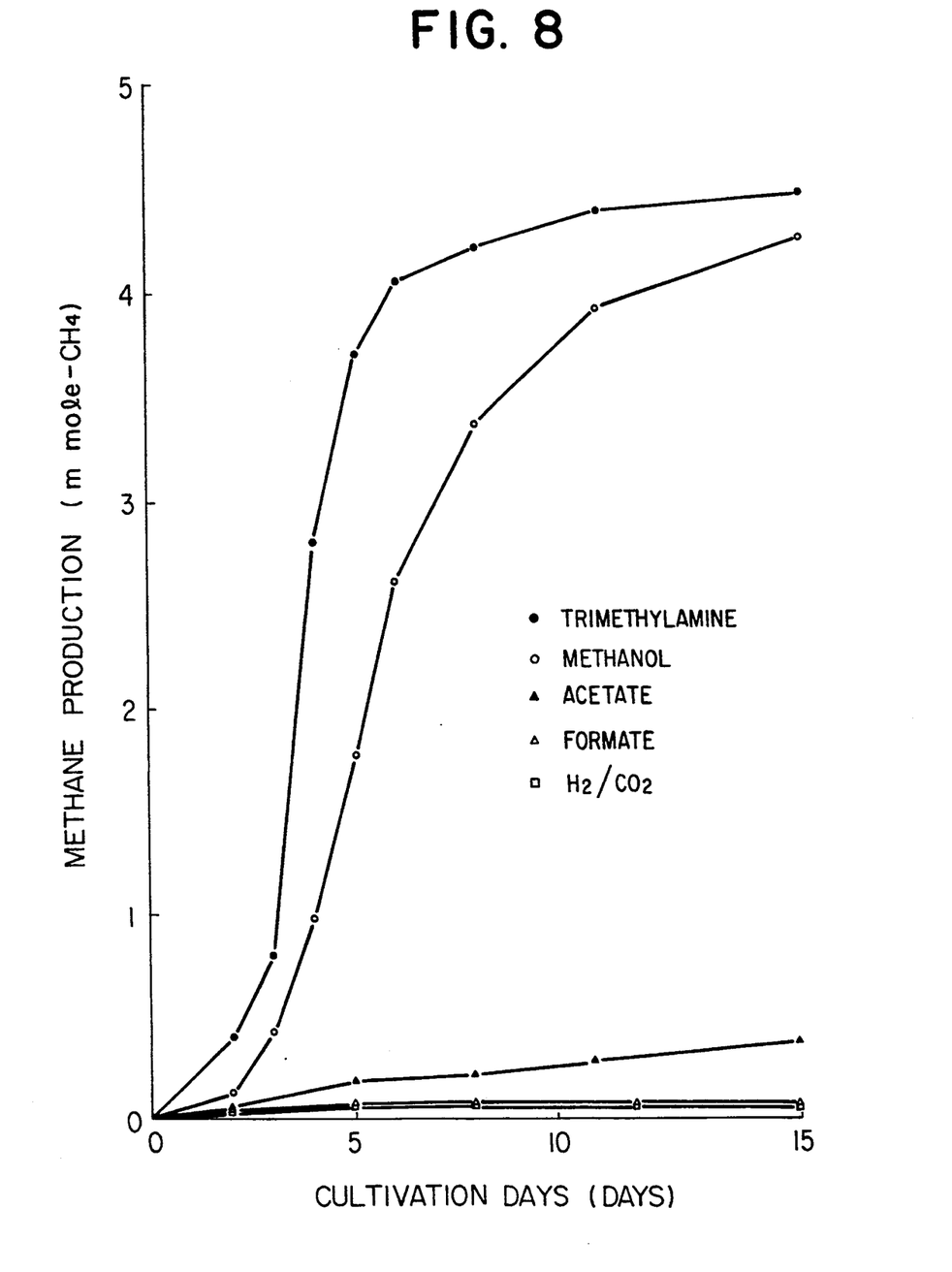

This Example was carried out to examine the influence of the kinds of substrates used on the amount of methane gas generated by the bacteria NY-844 of the present invention collected in the manner as discussed above, when cultured in a culture medium whose composition was as shown in Table I and in which the substrate used was one member selected from the group consisting of sodium formate, sodium acetate, methanol, trimethylamine and $H_2/CO_2$. In these cases, the gas phase for culture was $N_2$ (2 atms.; positive) except for the case where $H_2/CO_2$ was used as the substrate. When the substrate was $H_2/CO_2$, it was not added to the culture medium but was used as the gas phase (2 atms.; positive). In this Example, the pH was 7.8, the sodium chloride concentration was 3M and the cultivation temperature was 37° C.

The results obtained are plotted in FIG. 8, with the cultivation days as the abscissa and the amount of methane gas (m mole) generated as the ordinate and are also summarized in Table IV given below.

EXAMPLE 2-5

The bacteria NY-844 of the present invention were cultured in a culture medium whose composition was as shown in Table I and in which the substrate was 0.8% trimethylamine. Then, the generation time thereof was estimated from the amount of methane gas generated and it was found to be 5 to 10 hours.

In order to make it clear that the highly halophilic methane producing bacteria of the present invention are novel methane producing bacteria which can clearly be distinguished from known ones, properties of the bacteria NY-218 and NY-844 such as assimilation of substrates, morphological features, gram-staining properties, generation time, optimum growth temperature, optimum growth pH and optimum growth sodium chloride concentration are summarized in Table IV in comparison with those of the known methane producing bacteria.

218 of the present invention are novel methanogenic bacteria belonging to new genus Methanohalococcus (i) The methanogenic bacteria NY-218 of the present invention are extremely halophilic methanogen having an optimum growth sodium chloride concentration higher than that of the known methanogenic bacteria.

(ii) There is not conventionally known any methanogenic bacteria which simultaneously exhibit alkalophilic and halophilic properties. On the contrary, the methanogenic bacteria NY-218 of the invention are extremely halophilic and alkalophilic.

(iii) There is not conventionally known any halophilic or alkalophilic methanogenic bacteria which show methane gas production activity even at low temperatures of the order of 15° to 20° C. However, the methanogenic bacteria NY-218 of the present invention can withstand such low tempera-

TABLE IV

| Name of Bacteria | Substrate Assimilation Properties | | | | | | | | |
|---|---|---|---|---|---|---|---|---|---|
|  | $H_2/CO_2$ | HCOO—Na | Na-acetate | MeOH | Trimethyl amine | Morphology | Gram-Stain | Motility/Flagella | Generation time (hr) |
| (a) Known halophilic methane producing bacteria | | | | | | | | | |
| Halomethanococcus SLP 1) | — | — | — | + | + | coccus | — | —/— | |
| Methanococcus halophilus 2) | — | — | ± | + | + | coccus | | —/— | |
| Methanogenic bacterium SFI 3) | — | — | — | + | + | coccus | | —/— | 10.2 |
| (b) Known alkalophilic methane producing bacteria | | | | | | | | | |
| Methanobacterium alcaliphilum WeN$_4$ 4) | + | — | — | — | — | bacillus | — | —/— | |
| Methanobacterium thermo-alcaliphilum Ac60 5) | + | — | — | — | — | bacillus | | —/— | |
| (c) Bacteria of the Present Invention | | | | | | | | | |
| Methanohalococcus, alcaliphilum NY-218 | — | — | ± | + | + | coccus | — | +/+ | 5 to 10 |
| Methanohalococcus, alcaliphilum NY-844 | — | — | ± | + | + | coccus | — | +/+ | 5 to 10 |

| Name of Bacteria | Substrate Assimilation Properties | | | |
|---|---|---|---|---|
|  | Optimum Temp. (°C.) | Optimum pH | NaCl (M) | DNA G + C content (mol. %) |
| (a) Known halophilic methane producing bacteria | | | | |
| Halomethanococcus SLP 1) | 35 to 37 | 7.5 | 2.0 | 49 |
| Methanococcus halophilus 2) | 26 to 36 | 6.5 to 7.4 | 1.2 | 38 |
| Methanogenic bacterium SFI 3) | 37 | 7.4 | 2.1 | 41 |
| (b) Known alkalophilic methane producing bacteria | | | | |
| Methanobacterium alcaliphilum WeN$_4$ 4) | 37 | 8.1 to 9.1 | | 57 |
| Methanobacterium thermo-alcaliphilum Ac60 5) | 58 to 62 | 7.5 to 8.5 | | 39 |
| (c) Bacteria of the Present Invention | | | | |
| Methanohalococcus, alcaliphilum NY-218 | 35 to 37 (15 to 45) | 8.0 to 8.5 (7.0 to 9.0) | 2.5 to 3 | 42 |
| Methanohalococcus, alcaliphilum NY-844 | 35 to 37 (15 to 45) | 7.5 to 8.0 (6.5 to 8.5) | 2.5 to 3 | 43 |

*In Table IV, the numerals given in the parenthesis indicate the ranges in which the bacteria can grow.
1) See Applied and Environmental Microbiology, 1985, Vol. 50, No. 4, pp. 877–881.
2) See Microbiology (U.S.S.R.), 1983, Vol. 52, pp. 290–297.
3) See Applied and Environmental Microbiology, 1985, Vol. 50, No. 1, pp. 140–143.
4) See International Journal of Systematic Bacteriology, 1986, Vol. 36, No. 3, pp. 380–382.
5) See Archives of Microbiology, 1985, Vol. 142, pp. 211–217.

As seen from the results listed in Table IV, it is found, in the light of the following facts, that the bacteria NYtures and exhibit the methane production activity even at temperatures ranging from 15° to 20° C.

(iv) All the known alkalophilic methanogenic bacteria are not coccus but bacillus. Nevertheless, the methanogenic bacteria NY-218 of the present invention are coccus.

(v) There is not conventionally known any alkalophilic methanogenic bacteria which have the ability to assimilate substrates other than hydrogen. Nevertheless,—the methanogenic bacteria NY-218 of the invention can assimilate at least methanol and methylamine as a substrate.

(vi) The methanogenic bacteria NY-218 is different from previously reported moderately or extremely halophilic methanogens in its ability to grow at higher pH and the presence of flagella.

Likewise, it is found, from the following facts, that the bacteria NY-844 of the present invention are novel methanogenic bacteria belonging to new genus Methanohalococcus:

(i) No highly halophilic methanogenic bacteria is conventionally known. However, the methane producing bacteria NY-844 of the invention are extremely halophilic and have an optimum sodium chloride concentration higher than that of the known methanogenic bacteria;

(ii) All of the known halophilic methanogenic bacteria have an optimum growth pH ranging from 7.0 to 7.5. On the contrary, the highly halophilic methanogenic bacteria NY-844 of the present invention have the optimum growth pH ranging from 7.5 to 8.0, in other words they have a pH-dependency different from that of the known ones and unlike the known methane producing bacteria they maintain high activity even at higher pH.

(iii) There is not conventionally known any highly halophilic methanogenic bacteria which show methane gas production activity even at low temperatures on the order of 15° to 20° C. However, the methanogenic bacteria NY-844 of the present invention can withstand such low temperatures and exhibit the methanogenic activity even at temperatures of 15° to 20° C.

(iv) The methanogenic bacteria NY-844 is different from previously reported moderately or extremely halophilic methanogens in its ability to grow at higher pH and the presence of flagella.

Methanogenic bacteria are used as the microorganisms playing central role in the methane. fermentation (bio-methanation) widely employed for the purposes of efficient use of biomass and biological gas production. If the novel methane producing bacteria of the present invention are applied to the industrial methane fermentation technique, such a technique would make rapid progress since the bacteria of the present invention exhibit properties such as extremely halophilic and alkalophilic properties as well as resistance to low temperature. More specifically, the methods of methane fermentation are commonly carried out at around neutral pH region, a medium temperature of the order of 37° C. and a low salt concentration, but it becomes possible to carry out the methods at an alkaline pH, a high salt concentration and a lower temperature by using the methane producing bacteria of the invention. This, in turn, makes it possible to use a wide variety of biomass waste in such a method of methane fermentation.

Moreover, the conventional method of methane fermentation must be effected in the vicinity of a neutral pH and for this reason, a large amount of pH adjusting agents are in general added to a bioreactor. As a result, it is sometimes observed that the methane fermentation would possibly be inhibited because of the presence of a large amount of salts in the bioreactor. Such a disadvantage may effectively be eliminated by the use of the methane producing bacteria of the invention.

In addition, if the methane producing bacteria of this invention are used in breeding by a genetic engineering technique, as the source of genes coding properties favorable or resistant to special environments, such as halophilic and alkalophilic properties and resistance to low temperature, it would be possible to effectively carry out the practical methane fermentation or to efficiently produce other useful substances.

What is claimed is:

1. A method of using a biologically pure culture of Methanohalococcus alcaliphilum having an optimum growth sodium chloride concentration of from about 2.5M to about 3.0M and an optimum growth pH ranging from about 8.0 to about 8.5, and having methane production activity up to pH's of at least about pH 8.5, to produce methane, comprising culturing said culture of Methanohalococcus alcaliphilum in an anaerobic medium for a time sufficient to produce methane.

2. The method of claim 1, wherein said Methanohalococcus alcaliphilum has the identifying characteristics of NY-218.

3. The method of claim 1, wherein said Methanohalococcus alcaliphilum has the identifying characteristics of NY-844.

* * * * *

UNITED STATES PATENT AND TRADEMARK OFFICE
CERTIFICATE OF CORRECTION

PATENT NO. : 5,350,684
DATED : September 27, 1994
INVENTOR(S) : Naoki NAKATSUGAWA, et al.

It is certified that error appears in the above-indentified patent and that said Letters Patent is hereby corrected as shown below:

On the title page, Item [73], the third Assignee is spelled incorrectly. It should read:

--Rikagaku Kenkyusho--

Signed and Sealed this

Twentieth Day of December, 1994

Attest:

BRUCE LEHMAN

*Attesting Officer*     *Commissioner of Patents and Trademarks*